US 6,698,045 B1

(12) United States Patent
Coppens et al.

(10) Patent No.: US 6,698,045 B1
(45) Date of Patent: Mar. 2, 2004

(54) ANGLING HEAD IMMOBILIZATION DEVICE

(75) Inventors: Daniel D. Coppens, Avondale, PA (US); John A. Crowell, Wilmington, DE (US); Gary Gearon, Shohola, PA (US); John Damon Kirk, Ramsey, NJ (US); David M. Rabeno, Bear, DE (US); Thomas R. Winward, New Castle, DE (US)

(73) Assignee: Anholt Technologies, Inc., Avondale, PA (US)

( * ) Notice: Subject to any disclaimer, the term of this patent is extended or adjusted under 35 U.S.C. 154(b) by 0 days.

(21) Appl. No.: 10/287,063

(22) Filed: Nov. 4, 2002

Related U.S. Application Data

(60) Provisional application No. 60/336,303, filed on Nov. 2, 2001.

(51) Int. Cl.[7] ................................................ A61G 13/12
(52) U.S. Cl. .............................. 5/637; 5/622; 128/869; 606/130
(58) Field of Search ........................... 5/622, 637, 640, 5/643, 601; 128/869, 870, 845, 846, 857; 606/130

(56) References Cited

U.S. PATENT DOCUMENTS

| | | | | | |
|---|---|---|---|---|---|
| 4,256,112 | A | * | 3/1981 | Kopf et al. | 5/637 |
| 4,504,050 | A | * | 3/1985 | Osborne | 5/637 |
| 4,979,519 | A | * | 12/1990 | Chavarria et al. | 5/637 |
| 5,207,716 | A | * | 5/1993 | McReynolds et al. | 5/637 |
| 5,775,337 | A | * | 7/1998 | Hauger et al. | 128/869 |
| 5,832,550 | A | * | 11/1998 | Hauger et al. | 5/622 |
| 5,848,449 | A | * | 12/1998 | Hauger et al. | 5/601 |
| D462,448 | S | * | 9/2002 | Huttner | D24/191 |
| 6,442,777 | B1 | * | 9/2002 | Pauli | 5/622 |

* cited by examiner

*Primary Examiner*—Alexander Grosz
(74) *Attorney, Agent, or Firm*—Huntley & Associates LLC

(57) ABSTRACT

A portable, adjustable and angling head immobilization device for accurately and repeatably positioning a patient's head.

16 Claims, 3 Drawing Sheets

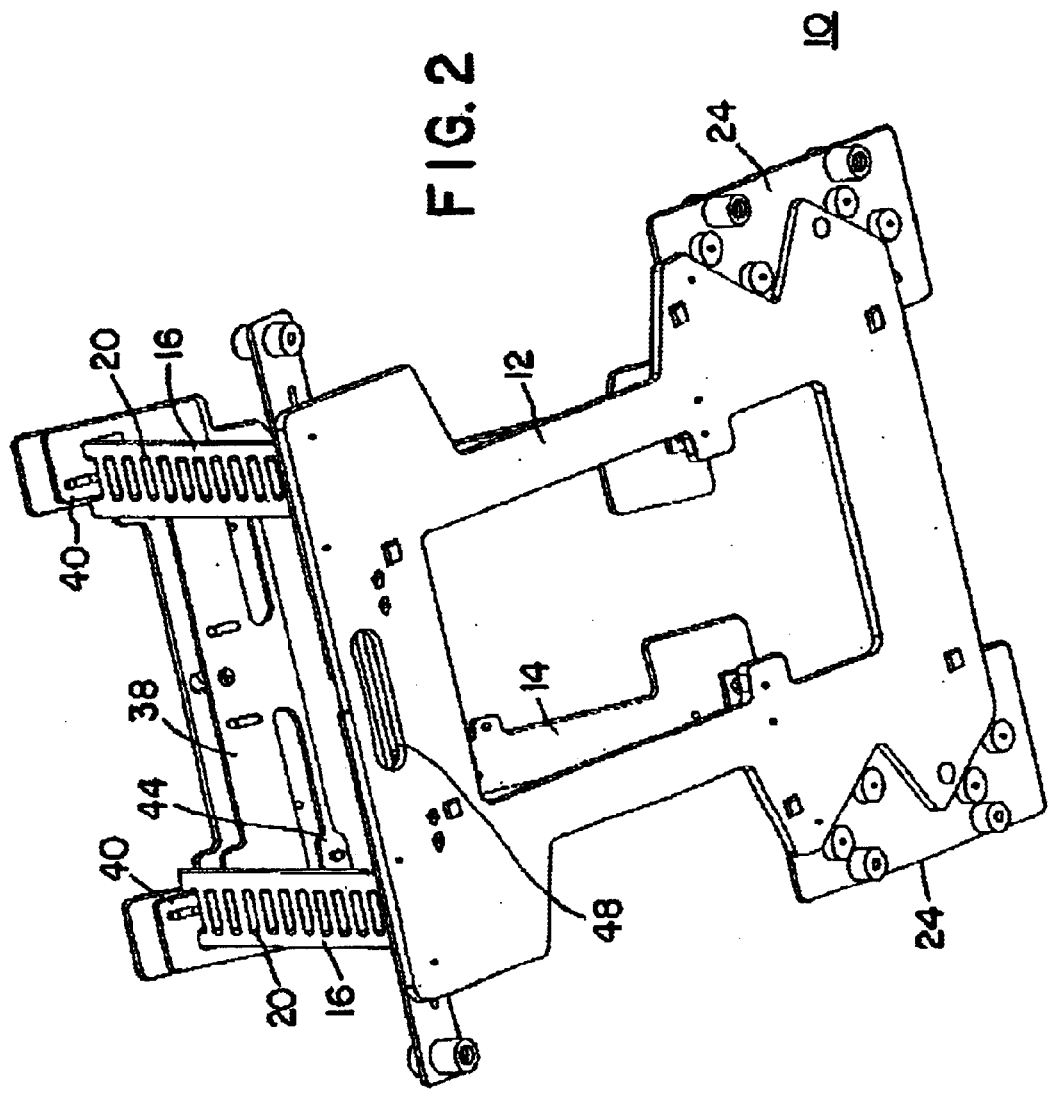

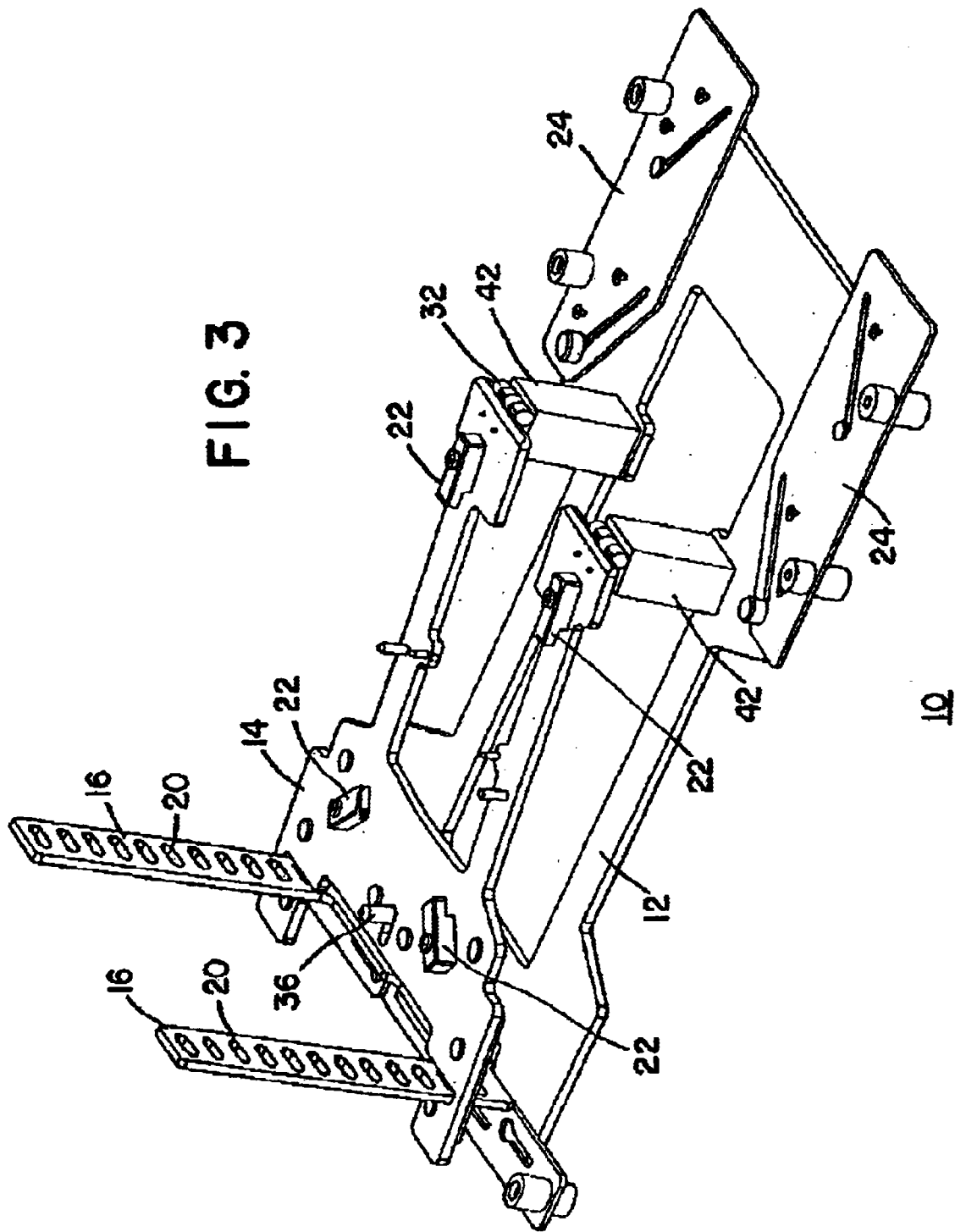

ANGLING HEAD IMMOBILIZATION DEVICE

CROSS-REFERENCE TO RELATED APPLICATIONS

This application claims the benefit of U.S. Provisional Application No. 60/336,303, filed Nov. 2, 2001.

BACKGROUND OF THE INVENTION

The present invention relates to a portable, adjustable and angling head immobilization device. The immobilization device of the present invention has several applications where adjustability and immobility of the head is required. The present invention is uniquely adjustable and is capable of being angled between −15 and 45 degrees with respect to horizontal thereby accommodating patients in various postures in both the prone and supine position.

A major application of the present invention can be for patients in treatment settings who require radiation treatment of cancer within the brain and neck. When a high energy beam is used for irradiation of the tumor, it is critical that the beam destroys the tumor but not the surrounding healthy tissue. In order to accomplish this objective with acceptable precision, it is critical that the head and neck be maintained in a precise and fixed position with no possibility of movement. Specifically, with the patient in the prone position, the present invention can be used to position the patient during the cranio-spinal axis technique. This technique requires that the patient's head is angled prone with an upward tilt geometry, which allows the radiation to exit inferior to the jaw instead of exiting through the jaw. The present invention can also be used to position the patient in the supine position. In this use, the present invention can be used for pituitary gland treatment. In this procedure, the patient's head is angled for proper geometry so as to prevent the exit of the radiation beam through the eyes. The present invention can also be used flat or at the 0-degree position in order to treat the patient's entire brain as well as neck region cancers.

There are immobilization devices on the market today with various deficiencies and shortcomings. Such deficiencies include lack of portability, difficulty in storing the device when not in use, incompatibility with available accessories or tables and difficulty in precisely and easily adjusting or angling the device. In addition, several patient positioning devices are not sufficiently radiolucent.

For example, several patient positioning devices contain metallic parts. In radiation therapy, metallic parts are not desirable, especially if they are in the treatment field. Metallic parts can cause increased elastic and inelastic radiation scattering as well as fluorescence which can expose the patient to unnecessary radiation. While the use of metals can cause unwanted radiation exposure, they can also reduce the desired radiation dose that reaches the target area due to their high radiation absorption compared to polymer and carbon fiber composites as in the present invention.

Some positioning devices are constructed of acrylic which provide lower strength to attenuation ratio than those constructed of carbon fiber composites. In addition, some positioning devices have cumbersome angling means, do not have interchangeable ladders or a slide lock mechanism that allows one handed operation and maneuverability. Furthermore, there are no commercial devices available that are collapsible and portable, or that allow a negative angle for prone positioning of the patient.

The present invention overcomes these deficiencies and provides mobility as well as precise and efficient adjustability in a light weight carbon fiber composite head immobilization device that is radiolucent.

SUMMARY OF THE INVENTION

The present invention provides a head immobilization device that is mobile and adjustable and is easily storable. The head immobilization device of the present invention can be constructed entirely of non-metallic components and provides exceptional radiolucency. Specifically, the present invention provides an angling head immobilization device for accurately and repeatedly positioning a patient's head comprising a base frame adaptable to be secured to a treatment table; at least one pivotable indexing ladder retentively and detachably secured to the base frame; a pivotable head rest frame secured to the base frame that is adapted to receive a head restraint device; and a slide locking mechanism with at least one index tab for use with the indexing ladder.

BRIEF DESCRIPTION OF THE DRAWINGS

FIG. 2 is an illustration of the slide lock mechanism of the present invention.

FIG. 3 is an illustration of a typical assembly of the present invention.

DETAILED DESCRIPTION OF THE INVENTION

Figure 1:
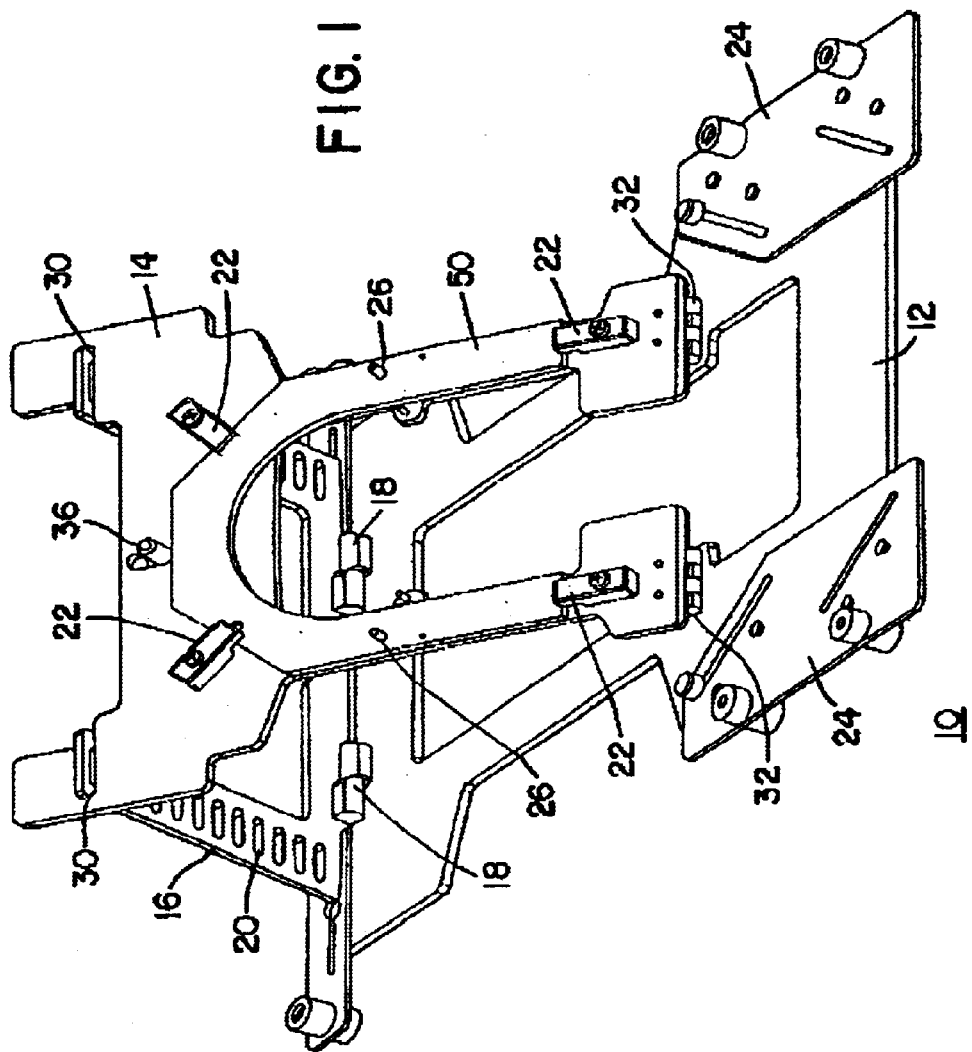
FIG. 1 is an illustration of a typical assembly of the present invention.

The present invention provides a radiolucent device that is easily adjustable and storable. Referring to the drawings, the head immobilization device of the present invention is designated by reference numeral 10. FIG. 1 shows the head immobilization device angled for use with a patient in the supine position. The head immobilization device of the present invention consists of a pivotable headrest frame 14 connected to a base frame 12. The headrest frame 14 is be attached by hinges 32 or any attaching means that allows the headrest frame 14 to pivot. In addition, the pivoting end of the headrest frame 14 can be equipped with adjustable or removable riser blocks 42 (shown in FIG. 3). The riser blocks 42 raise the pivot end of the headrest frame off of the base frame 12 and allow the headrest frame 14 to create a negative angle with respect to horizontal. This unique design makes the present invention more versatile and allows the patient to be positioned and treated in both the prone and supine positions.

An indexing ladder 16 is retentively and detachably secured to the base frame 12 by ladder pivot connectors 18. The indexing ladder is interchangeable and can contain varying number and size of ladder indexing slots 20 depending upon the desired precision and angle of the headrest frame 14. The pivotable headrest frame 14 contains securing clips 22 for attaching the head restraint assembly (not shown). The head restraint assembly comprises a U-shaped insert 50 as well as a deformable mesh sheet or patient mask. The securing clips can be rotated in order to clamp the head restraint assembly to the headrest frame 14. Although the figure depicts rotating clips, the present invention contemplates several attaching means including snap clips that are sufficient to securely affix the head restraint assembly to the headrest frame 14. Snap clips allow the head restraint assembly to be pressed down and snapped into place in one fluid movement. The headrest frame also includes at least one guide pin 26 for precisely and repeatably positioning the head restraint assembly to the headrest frame 14. The headrest frame 14 has at least one cutout 30 at one end to slidably fit over the indexing ladder 16. A slide lock mechanism 38 (shown in FIG. 2) is attached to the headrest frame 14. A movable slide post 36 is connected to the slide lock mechanism 38 and protrudes through the headrest frame 14 for operating the slide lock mechanism 38.

The headrest frame 14 is adaptable for receiving and fixing the head restraint assembly, which includes a U-shaped insert 50. The U-shaped insert 50 is used in conjunction with the deformable mask (not shown). The insert 50 secures the mask and allows the mask to be securely attached to the headrest frame 14. The device of the present invention can also include at least one removable guide post for receiving the insert 50 and allowing the mask to slide down the post over the patient's face until secured to the headrest frame 14. The removable guide posts aid in the formation of the patient mask by precisely positioning the head restraint assembly and evenly sliding the deformable mask over the patient's head.

The head immobilization device of the present invention 10 can be attached to any standard patient table or couch by a securing mechanism 24. The securing means can be a removable device as depicted in FIG. I or it can be integrated into the base frame 12 with appropriately placed holes and pins so that it universally fits most common patient tables.

As seen in FIG. 2, the slide lock mechanism 38 is attached to the underside of the headrest frame 14 and can slide up and down in order to insert the indexing tabs 40 into the indexing slots 20. The unique configuration of the slide lock mechanism 38, includes the slide lock arms 44. The slide lock arms 44 securely fix the lower end of the mechanism 38 to the headrest frame 14 while allowing the top end to resistively slide up and down. The slide lock arms 44 provide elastic movement and cause the slide lock mechanism 38 to return to its original configuration when released. The slide post 36 operates the slide lock mechanism 38, which in turn changes the position of the index tabs 40. With the index tabs 40 inserted into the index slots 20, the headrest frame 14 is locked into position with the indexing ladder 16. This unique configuration provides a built in safety feature in that the headrest frame 14 is locked into place and cannot unintentionally collapse. In addition, with the index tabs 40 inserted into the index slots 20, the headrest frame 14 is locked into position with the indexing ladder 16 and the ladder is prevented from becoming disengaged and falling forward or backward. With the index tabs 40 retracted, the headrest frame pivots freely and the indexing ladder slides through the cutout 30 in the headrest frame 14. This way the angle is easily, accurately and repeatably adjusted. The unique design of the present invention allows for quick and easy adjustment and one-handed operation.

When treatment is complete, the device can be folded flat by inserting the indexing ladder 16 into the cutouts 30 in the headrest frame 14 and allowing the headrest frame 14 to lay flat. The indexing ladder can then be folded flat on top of the headrest frame 14. A carrying slot 48 can be machined into the base frame 12 to aid in transporting the device.

It is understood that that the dimensions may vary from that shown in the drawings and the drawings are presented for illustrative purposes only. The precise shapes and dimensions of the invention can be changed without departing from the object of the present invention.

The head immobilization device of the present invention is adjustable in at least two ways. First, the mechanism that locks the head immobilization device to the table is adjustable. This adjustability provides complete flexibility in that the device of the present invention is self-contained and fits all existing procedure tables. There is no need for retrofitting or additional clamping or securing means. The head immobilization device of the present invention adjusts on both sides and can easily be centered on a procedure table because of its two-way adjustability.

The immobilization device has an angle positioning and locking mechanism that allows fixed, repeatable and incremental changes in the angle at which the head rests. The mechanism which locks and unlocks the headrest frame 14 at the desired angle is easily adjustable with one hand which results in exceptional ease of use. This particular feature allows faster procedures lessening the cost of the procedure and the discomfort to the patient.

All components of the present invention can be non-metallic although some metallic parts can be used if they do not disrupt the performance of the device. Performance of the device is directly influenced by the material used for its construction. Lighter elements are preferred over heavier elements. For example, the lighter elements in composites and polymer materials result in less elastic and inelastic radiation scattering compared to materials containing metals or alloys. In addition, fluorescence is reduced. When a metal atom is impacted by radiation, it absorbs the radiation energy by ejecting an electron from its shell in the atom's electron cloud. When an electron falls back into the shell, radiation is emitted. This effect is known as fluorescence. Because the radiation can be emitted in any direction, the patient is subjected to an undirected dose of radiation energy. Metals are also undesirable due to their high radiation absorption compared to plastics and carbon composite. This also reduces the therapy dose available to the patient.

The individual components can be selected based on the intended use of the device but typically are crafted out of materials that provide exceptional radiolucency, such as carbon composite. This particular feature is especially important if a highly oblique angle must be used for treating the patient where the device could come into the line of the high-energy beam. A radiolucent device allows imaging and treatment of a patient through the head immobilization device. This increases the treatment flexibility by allowing an accurate attack of the cancer or tumor from all aspects and angles.

The device of the present invention is easily portable and storable and collapses to a flat configuration. The device can be folded flat and locked in place when not in use so that it occupies little storage space. The device can also be configured with a handle and can be easily carried in one hand like a brief case. The portability of the present device is further enhanced by the efficient design and construction from lightweight materials including carbon fiber face sheets.

The present invention can be used in conjunction with any available tables as well as any available accessories that can be used with the immobilization device. One such accessory is a readily available deformable low temperature thermoplastic mask. One such product is a specialty mask currently sold by WFR/Aquaplast which can be attached to the present invention. The thermoplastic mesh mask is formed to fit the patient's features and dimensions and is attached to the headrest frame 14 in order to restrict the patient's movement and accurately and repeatably position the patient for treatment.

The Aquaplast RT mesh mask is composed of polycaprolactone sheet that has been cross-linked to achieve the required handling properties. It can be produced in various thicknesses between 1 and 5 mm. The material softens and becomes moldable at 140 degrees Fahrenheit. This is usually achieved by immersing the Aquaplast RT in hot water. The Aquaplast RT is then removed from the water, blotted dry and then molded over the patient's body part that is undergoing radiation therapy cancer treatment. As the Aquaplast RT cools it solidifies into a rigid plastic shell. This shell can then be removed from the patient and then re-applied prior to subsequent treatments to ensure that the patient is positioned the same.

It is generally easier to handle and secure softened Aquaplast RT if it is attached to a frame made from a material that stays rigid in hot water. Disposable U-frames are high temperature ABS plastic U-shaped frames that have Aquaplast RT bonded inside the U frame. As the frame is immersed in hot water, the Aquaplast RT softens leaving the ABS U shaped frame rigid and maneuverable. The ABS frame is then secured to the baseplate with various attaching means including swivel locks or retention clips. After treatment, the entire mask is discarded. An alternative is loading an Aquaplast RT sheet into a reusable frame. The reusable frame can be separated from the Aquaplast RT after the final treatment. The Aquaplast RT portion is then discarded while the U portion is retained and can be reused.

In using the angling head immobilization device of the present invention, the patient can be treated in the prone or supine position. When treating the patient in the prone position, a custom facemask must be prepared. In order to make the custom mask, the patient is placed in a supine position. The Aquaplast RT is softened by immersion in hot water. The softened mask is then pre-stretched and draped downward onto the patient's face while the U frame is suspended in front of the patient's head. The Aquaplast RT is allowed to harden while contoured to the patient's face. The hardened facemask is then turned over and secured to the headrest frame. The headrest frame is angled appropriately for the particular treatment. The patient is then positioned face down in the custom mask in the prone position. In addition, the patient may be further adjusted and positioned with various cushions such as a vacuum cushion or solid positioning table. Once positioned, a second mask is pre-stretched and placed over the posterior of the patient's head. Once contoured and hardened, the second mask is secured to the headrest frame and the patient's head is encased and immobilized and ready for treatment.

This description and the Figures illustrate one example of the present invention and are in no way meant to be limiting. Several different specific designs are contemplated by the inventors without parting from the original scope of the present invention and would be easily recognizable by those skilled in the art. Whereas the invention has been shown and described in connection with the preferred embodiments thereof, it will be understood that many modifications, substitutions and additions can be made which are within the intended broad scope of the following claims.

We claim:

1. An angling head immobilization device for accurately and repeatably positioning a patient's head, comprising:
   a base frame adaptable to be secured to a treatment table;
   at least one pivotable indexing ladder retentively and detachably secured to the base frame;
   a pivotable headrest frame secured to the base frame that is adapted to receive a head restraint assembly; and
   a slide locking mechanism with at least one index tab for use with the indexing ladder.

2. An angling head immobilization device of claim 1, wherein the pivotable indexing ladder has a plurality of slots therein for receiving the at least one index tab.

3. An angling head immobilization device of claim 1, wherein the pivotable headrest frame is adaptable for receiving a head restraint assembly, the head restraint assembly comprising a U-shaped insert and a deformable mesh sheet attached thereto, that is capable of forming a mask over a patient's head.

4. An angling head immobilization device of claim 1, wherein the at least one indexing ladder and the pivotable headrest frame can fold flat with the base frame.

5. An angling head immobilization device of claim 1, wherein the pivotable headrest frame has at least one guide pin for positioning the mask to the pivotable headrest frame.

6. An angling head immobilization device of claim 5 wherein the pivotable headrest frame has at least one securing clip for locking the head restraint assembly to the pivotable headrest frame.

7. A head positioning device of claim 1 wherein the pivotable headrest frame has at least one removable guide post for receiving the head restraint assembly while forming the patient mask.

8. A head positioning device of claim 1, wherein the base frame has at least one adjustable riser block, wherein the pivotable headrest frame has a pivot end and an indexing end and the pivot end is secured to the at least one riser block.

9. An angling head immobilization device of claim 8 wherein the pivotable headrest frame can be indexed between about −15 and 45 degrees with respect to horizontal.

10. An angling head immobilization device of claim 9 for accommodating a patient in a prone position.

11. An angling head immobilization device of claim 1 wherein the angling head immobilization device is radiolucent and allows imaging and treatment of a patient through the head immobilization device.

12. An angling head immobilization device of claim 1 adaptable for use in patient imaging and treatment including diagnostic imaging of the head and neck, whole brain tumor treatments, treatment of tumors in the neck region, craniospinal axis technique and pituitary gland treatment.

13. An angling head immobilization device of claim 1, wherein the device is made from carbon composite.

14. An angling head immobilization device of claim 1, wherein the pivotable headrest frame has at least one cutout to slidably fit over the indexing ladder.

15. An angling head immobilization device of claim 14, wherein the pivotable headrest frame further comprises a slide locking mechanism for releasably locking the pivotable headrest frame to the indexing ladder, wherein the slide locking mechanism has at least one indexing tab and the indexing ladder has at least one slot for slidably receiving the indexing tab.

16. An angling head immobilization device of claim 15, wherein at least one movable slide post is connected to the slide locking mechanism for retracting the at least one indexing tab, and wherein the slide locking mechanism is capable of one-handed operation.

* * * * *